United States Patent [19]

Pincus

[11] Patent Number: 5,583,004
[45] Date of Patent: Dec. 10, 1996

[54] DIRECT DETECTION OF UNEXPECTED ALLOANTIBODIES IN THE SERUM OF PROSPECTIVE TRANSFUSION RECIPIENTS USING A NEW HEMAGGLUTINATION INHIBITION ASSAY

[76] Inventor: Mathew R. Pincus, 135 Eastern Pkwy., Brooklyn, N.Y. 11238

[21] Appl. No.: 363,754

[22] Filed: Dec. 23, 1994

[51] Int. Cl.$^6$ ................................ G01N 33/53
[52] U.S. Cl. ............ 435/7.25; 435/7.21; 435/962; 436/512; 436/513; 436/518; 436/520; 436/536; 436/540; 436/819
[58] Field of Search ............... 435/7.25, 7.21, 435/962; 436/512, 513, 518, 520, 819, 536, 540; 424/11

[56] References Cited

U.S. PATENT DOCUMENTS

| | | | |
|---|---|---|---|
| 4,275,053 | 6/1981 | Rosenfield et al. | 424/12 |
| 4,328,183 | 5/1982 | Rosenfield et al. | 422/57 |
| 4,436,825 | 3/1984 | Lalezari | 436/520 |
| 4,587,222 | 5/1986 | Guffroy | 436/509 |
| 4,607,009 | 8/1986 | Steplewski et al. | 435/7 |
| 4,764,465 | 8/1988 | Foung et al. | 435/172.2 |
| 4,868,109 | 9/1989 | Lansdorp | 435/28 |
| 5,071,774 | 12/1991 | Vorpahl et al. | 436/501 |
| 5,213,963 | 5/1993 | Uthemann | 435/7.25 |
| 5,283,178 | 2/1994 | Kessler et al. | 435/7.25 |
| 5,302,512 | 4/1994 | Pernelle | 435/7.25 |
| 5,401,636 | 3/1995 | Craig | 435/7.21 X |

OTHER PUBLICATIONS

Technical Manual of the American Association of Blood Banks, 8th edition, 1981, Chapter 13, "Detection and Identification of Red Blood Cell Antibodies", pp. 177–205.

I. Shulman, "Safety in Transfusion Practices: Red Cell Compatibility Testing Issues," in Clinics in Laboratory Medicine 12(4):685–700, 1992.

L. Petz, "Transfusing the Patient with Autoimmune Hemolytic Anemia," in Clinics in Laboratory Medicine 2(1)193–210.

*Primary Examiner*—Carol A. Spiegel
*Attorney, Agent, or Firm*—Graham & James LLP

[57] ABSTRACT

Human red blood cells with antigenic determinants recognized by unexpected alloantibodies are mixed with serum from the potential recipient. Following incubation, multivalent monoclonal IgM antibodies specific to the antigenic determinant present on the test red blood cells are added. If the recipient's serum is negative for an unexpected antibody which would bind to the antigens present on the test red blood cells, then the multivalent antibody will agglutinate the red cells. Conversely, if an unexpected antibody specific to those determinants is present in the recipient's serum, hemagglutination will be inhibited.

7 Claims, No Drawings

DIRECT DETECTION OF UNEXPECTED ALLOANTIBODIES IN THE SERUM OF PROSPECTIVE TRANSFUSION RECIPIENTS USING A NEW HEMAGGLUTINATION INHIBITION ASSAY

This application relates to screening blood for use in transfusions. More particularly, this application relates to a technique for detecting the presence of unexpected antibodies in blood of prospective blood transfusion recipients.

BACKGROUND OF THE INVENTION

Perhaps the most significant obstacle to overcome in successfully transfusing blood from a donor to a recipient is the detection of untoward immune responses. In particular, immune reaction of the recipient against the donor's blood can have life-threatening consequences for the recipient. Immune reactions between antigens present in the blood of the donor and antibodies against these antigens in the recipient can cause severe hemolysis, renal failure, and shock.

Examples of well-known and clinically significant antigens in blood are the A and B antigens of the ABO System. These antigens are present on the red blood cells which carry oxygen in the body. In order that transfusion occur successfully, it is imperative that the recipient not have antibodies directed to antigens present on donor blood cells. An immune reaction by the recipient of a transfusion of donor cells results in destruction of the donor cells with possible catastrophic damage to the kidneys and other organs.

Other antigens present on the surfaces of human red blood cells are also known; some of these can cause serious immune responses when transfused into patients with antibodies to them. The term "unexpected alloantibodies" is used to refer to antibodies to antigens on the surface of human red blood cells, other than the A, B or Rh antigens. American Association of Blood Banks Technical Manual, p. 333 (1993)("AABB Tech,. Manual"). While the A and B antigens are carbohydrate, the antigens to which unexpected alloantibodies are directed are proteins.

At present a number of systems of unexpected alloantibodies are known. The Lutheran, Kell, Duffy and Kidd systems are representative. Each of these systems has a number of allotypes. For example the Lutheran blood group system may display a or b antigens or both. Id. at 266. The Kell system includes at least three different antigens, which may be genetically linked. Id. at 268. The Duffy system includes two antigens, while the Kidd system includes two.

Because reaction between unexpected alloantibodies in the recipient and target antigens in the donor blood can have serious, clinical consequences, it is imperative to develop rapid and sensitive assays for unexpected antibodies. At present, unexpected antibodies are detected by laborious, and time-consuming testing of donor serum against panels of red blood cells with known antigenic determinants.

In the technique presently employed, the recipient's sera is mixed with human red blood cells known to display antigens from one or more blood group systems. The presence of an unexpected alloantibody bound to the test cells is demonstrated by observing hemagglutination following addition of an antibody to human immunoglobulin. Because the unexpected alloantibody could bind to any of a number of different antigens present on the test red blood cells, identification of the particular antigen to which an unexpected alloantibody is directed requires that the recipient's serum be tested against samples of red blood cells which display different combinations of antigens. When more than one unexpected alloantibody is present in the serum of the recipient, the analysis becomes complex, necessitating study of multiple panels of red blood cells. AABB Manual, pp. 340–43. The sequential testing of the serum sample of a recipient against different combinations of test cells (referred to as panels) is expensive, time consuming and laborious.

The subject of this application is a novel assay which obviates much of the time-consuming panel testing of the prior art method. The invention takes advantage of monoclonal antibodies directed to the known antigens to which unexpected alloantibodies are directed.

SUMMARY OF THE INVENTION

Human red blood cells with antigenic determinants recognized by unexpected alloantibodies are mixed with serum from the potential recipient. Following incubation, multivalent monoclonal IgM antibodies specific to the antigenic determinant present on the test red blood cells are added. If the recipient's serum is negative for an unexpected antibody which would bind to the antigens present on the test red blood cells, then the multivalent antibody will agglutinate the red cells. Conversely, if an unexpected antibody specific to those determinants is present in the recipient's serum, hemagglutination will be inhibited.

DETAILED DESCRIPTION

The method of this invention permits reliable detection of unexpected alloantibodies in the blood of candidates for blood transfusion. The method requires human red blood cells known to be positive for an antigen that is recognized by an unexpected alloantibody.

At present, the unexpected alloantibodies comprises five blood group systems: Kell, Duffy, Kidd, Lutheran and that part of the Rh system which recognizes the C, c, E, e and K antigens. AABB Manual, chapter 15 "Identification of Unexpected Alloantibodies" pp. 333–55 (1993). The Kell system is presently understood to comprise the K and k antigens, $Kp^a$, $Kp^b$, $Js^a$ and $Js^b$. The Lutheran system is presently understood to include two antigens: $Lu^a$ and $Lu^b$. The Duffy system is presently understood to also include two antigens: $Fy^a$ and $Fy^b$. And the Kidd system is also presently understood to include two antigens: $Jk^a$ and $Jk^b$. Antibodies to each of these antigens has been detected in patients. AABB Manual, ch. 12 "Other Blood Groups," pp. 259–285.

Based on the racial background of the transfusion candidate, as well as clinical data, it is generally possible to identify potential blood group antigens that are of concern. AABB Manual, pp. 259–285. In the presently preferred embodiment of the present invention, human panel cells known to bear the antigen of interest are suspended in warm (37 degree) saline solution. Serum from the intended transfusion recipient is mixed to the suspended red blood cells, and the suspension is incubated to permit binding between unexpected alloantibodies in the serum and antigens on the surface of the red blood cells. A multivalent monoclonal antibody to the antigen under test (IgM is especially preferred) is added to the suspension and the suspension is again incubated.

If unexpected alloantibodies in the test serum specific to the antigens present on the test red blood cells are present, then the unexpected alloantibodies will bind to the cells. Multivalent monoclonal antibodies are used in this assay because they will cause the red blood cells to agglutinate if the red blood cells display an antigen to which the monoclonal antibody is specific. Because there are ten binding sites for the antigen for each molecule of IgM, a single molecule of IgM can attach to more than one red blood cell, resulting in clumping (hemagglutination) of the cells. However, If the antigens to which the unexpected alloantibodies are bound are the same as those to which the monoclonal would bind, then the binding of the monoclonal will be blocked and no clumping will occur.

Accordingly, the present assay affords a simple and specific assay for any of the antigens to which unexpected alloantibodies are directed. Although the method is described here for human blood transfusions, the method could be applied in veterinary contexts as well, providing that typed red blood cells and monoclonal antibodies are available.

In some instances unexpected alloantibodies in a patient's blood may be capable of directly agglutinating red blood cells bearing the target antigen. Assuming that it has been determined that the hemagglutination is due to the presence of an alloantibody rather than an autoantibody, a modification of the method of the present invention should then be used. Fab fragments of an antibody directed to the antigen under investigation are prepared. The Fab fragments can be mono or polyclonal in origin. In the first step of the modified assay, the red blood cells are exposed to the Fab fragments in order to partially block the antigenic sites. The method of the present invention is then carried out as previously described. Alternatively, the serum may be diluted before testing in order to reduce the titer of unexpected alloantibodies.

EXAMPLE

Control 1.

Sample 1 consists of a volume of 100 ul of a 3 percent suspension of panel cells (Gamma Biologicals, Inc., Houston, Tex.) known to be positive for the $Jk^a$ (Kidd) antigen is mixed with 100 ul of normal saline and mixed gently for 5 min. A volume of 100 ul of Bioclone (Ortho Diagnostics, Raritan, N.J.) monoclonal IgM anti-$Jk^a$ is then added to this suspension, and the resulting suspension is incubated at 27° for 5 min. and then centrifuged for several minutes. The contents are then resuspended, and the resulting suspension is graded on a scale of 1+ (weak) to 4+ (strong) for hemagglutination.

Control 2.

Sample 2 consists of the above experiment of Control 1, except that Bioclone polyclonal anti-$Jk^b$ antibody is substituted for the normal saline solution.

Test.

In sample 3, human anti-$Jk^a$ antiserum (Gamma Diagnostics) was used substituted for normal saline, to test for hemagglutination inhibition when an unexpected alloantibody (anti $Jk^a$) was present. This experiment was performed exactly as described in Control 1 except that 100 ul of the antiserum was substituted for the normal saline in Control 1. Also, an identical experiment with human anti-$Jk^b$ antiserum was performed as another negative control.

Results:

The results are summarized in Table I.

TABLE I

Hemagglutination with Different Samples and Antisera

| Sample | Hemagglutination Score |
| --- | --- |
| 1. Control 1 | 4+ |
| 2. Control 2 | 4+ |
| 3. Human anti-$Jk^a$ antiserum | 1–2+ |
| 4. Human anti-$Jk^b$ antiserum | 4+ |

Control 1 was positive because there are no blocking anti-$Jk^a$ antibodies present. Thus the monoclonal anti-$Jk^a$ IgM caused agglutination of the red blood cells by binding to the $Jk^a$ antigens.

Control 2 was positive again because anti-$Jk^b$ does not block $Jk^a$ sites on the panel cells.

Sample 3, the critical test sample was negative for hemagglutination because the anti-$Jk^a$ antiserum blocked the $Jk^a$ sites.

Sample 4 was positive for hemagglutination because anti-$Jk^b$ antiserum does not block $Jk^a$ sites.

The experimental data demonstrates that the method of this invention can be used to detect an antibody to the $Jk^a$ allotype of the Kidd system. The method is easily applicable to any other red cell antigen system for which patients' antisera do not of themselves cause hemagglutination. These include the Rh, Kidd, Duffy, Kell and Lutheran antigens.

While the invention has been set forth in terms of specific embodiments and examples, those embodiments and examples are for purposes of illustration only, and are not intended to limit the scope of applicant's invention, which is set forth in the claims appended hereto.

I claim:

1. A method for direct detection of an unexpected alloantibody to a preselected antigen, comprising:

(a) providing a red blood cell reagent comprising the preselected antigen as a cell surface antigen;

(b) incubating the red blood cell reagent with a serum sample to be tested for the unexpected alloantibody such that any of the unexpected alloantibody in the serum sample specifically binds to the preselected antigen on the red blood cell reagent;

(c) contacting the mixture of step b with a multivalent antibody which specifically binds to the preselected antigen; and (d) assessing any resulting hemagglutination, wherein a decrease or absence of hemagglutination relative to the hemagglutination resulting from contacting the red blood cell reagent and the multivalent antibody in the absence of the serum sample indicates the presence of the unexpected alloantibody in the serum sample.

2. The method according to claim 1 wherein the preselected antigen is an antigen selected from the Lutheran system, the Duffy system, the Kell system and the Rh system.

3. The method according to claim 1 wherein the multivalent antibody is a monoclonal antibody.

4. The method according to claim 1 wherein the multivalent antibody is a monoclonal antibody of the IgM class.

5. The method according to claim 1 further comprising contacting a Fab fragment which specifically binds to the preselected antigen with the red blood cell reagent prior to incubation with the serum sample, if step (b) results in hemaglutination.

6. The method according to claim 1 wherein the preselected antigen is selected from the group consisting of C, c, E, e, $Jk^a$, $Jk^b$, $Fy^a$, $Fy^b$, $Rp^a$, $Kp^b$, $Js^a$, $Js^b$, $Lu^a$ and $Lu^b$.

7. The method according to claim 1 wherein the serum sample is diluted prior to contact with the red blood cell reagent in step (b).

* * * * *